United States Patent [19]

Bartmann et al.

[11] 4,260,763
[45] Apr. 7, 1981

[54] ISOQUINOLINE ALDEHYDES

[75] Inventors: Wilhelm Bartmann; Elmar Konz, both of Bad Soden am Taunus; Hansjörg Kruse, Kelkheim, all of Fed. Rep. of Germany

[73] Assignee: Hoechst Aktiengesellschaft, Frankfurt am Main, Fed. Rep. of Germany

[21] Appl. No.: 20,410

[22] Filed: Mar. 14, 1979

[30] Foreign Application Priority Data

Mar. 16, 1978 [DE] Fed. Rep. of Germany ....... 2811361

[51] Int. Cl.³ .................... A61K 31/47; C07D 217/16
[52] U.S. Cl. ...................................... 546/144; 546/90; 546/141; 542/422; 424/258
[58] Field of Search ......................... 546/144; 424/258

[56] References Cited

U.S. PATENT DOCUMENTS

| | | | |
|---|---|---|---|
| 1,434,306 | 10/1922 | Miescher | 546/168 |
| 3,457,265 | 7/1969 | Seeger et al. | 546/144 |
| 3,891,654 | 6/1975 | Valette | 546/144 |

*Primary Examiner*—Donald G. Daus
*Assistant Examiner*—James H. Turnipseed
*Attorney, Agent, or Firm*—Curtis, Morris & Safford

[57] ABSTRACT

Isoquinoline-4-aldehydes of the formula

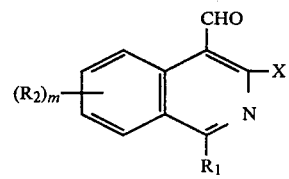

in which X denotes bromine or chlorine, $R_1$ is phenyl optionally mono- or disubstituted by halogen, hydroxy, nitro, amino, or amino substituted by one or two aliphatic, cycloaliphatic or aromatic hydrocarbon radicals having from 2 to 18 carbon atoms, the nitrogen atom possibly being included in a heterocyclic ring, acyl amino, alkyl or alkoxy each having from 1 to 6 carbon atoms, benzyloxy, or trifluoromethyl, or is pyridyl or thienyl;

$R_2$ is hydrogen, halogen, hydroxy, alkyl or alkoxy having from 1 to 6 carbon atoms, nitro, amino, benzyloxy, methylene dioxy or ethylene dioxy and m is 1 or 2;

which are effective in the treatment of spasms and as tranquilizers.

8 Claims, No Drawings

ISOQUINOLINE ALDEHYDES

This invention relates to novel, substituted isoquinoline aldehydes having valuable pharmacological, in particular psychotropic, properties.

It is the object of the invention to provide isoquinoline 4-aldehydes of the formula I

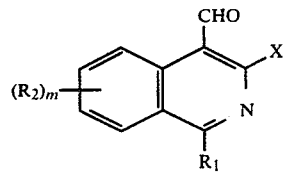

in which X denotes bromine or chlorine, $R_1$ is phenyl optionally mono- or disubstituted by halogen, hydroxy, nitro, amino, or amino substituted by one or two aliphatic, cycloaliphatic or aromatic hydrocarbon radicals having from 2 to 18 carbon atoms, the nitrogen atom possibly being included in a heterocyclic ring, acyl amino, alkyl or alkoxy each having from 1 to 6 carbon atoms, benzoyloxy, or trifluoromethyl, or is pyridyl or thienyl;

$R_2$ is hydrogen, halogen, hydroxy, alkyl or alkoxy having from 1 to 6 carbon atoms, nitro, amino, benzyloxy, methylene dioxy or ethylene dioxy and m is 1 or 2;

the physiologically tolerated salts thereof, processes for their manufacture, pharmacological preparations containing same and methods for their use.

Preferred compounds according to the invention are those in which X is chlorine, $R_1$ denotes a pyridyl ring or a phenyl ring which latter is mono- or disubstituted by hydroxy, halogen, nitro, amino or amino substituted by two identical aliphatic hydrocarbon radicals each having from 1 to 4 carbon atoms, alkyl or alkoxy each having from 1 to 4 carbon atoms, m is 1 or 2 and $R_2$ is hydrogen, halogen, alkyl or alkoxy having from 1 to 4 carbon atoms, or hydroxy.

Especially preferred compounds according to the invention are those in which X denotes chlorine, $R_1$ is a phenyl ring mono- or disubstituted by halogen, hydroxy, nitro, $C_1$-$C_3$ alkyl, amino or methoxy, m is 1 or 2 and $R_2$ denotes hydrogen, halogen, hydroxy, $C_1$-$C_3$ alkyl or methoxy.

To prepare a compound of formula I (a) a compound of formula II

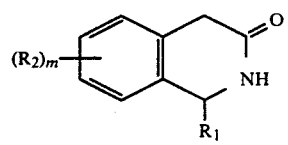

in which $R_1$, $R_2$ and m have the same meaning as in formula I is reacted with a Vilsmeier adduct of an acid amide, for example dimethyl formamide, diethyl formamide, N,N-methylphenyl formamide or N-formylpiperidine, and an acid chloride, for example phosphorus oxichloride, thionyl chloride, phosgene, or an acid bromide such as phosphorus oxibromide or phosphorus tribromide, to give a compound of formula III

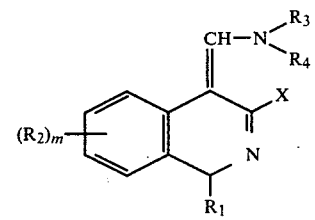

in which X is chlorine or bromine and $R_3$ and $R_4$ denote alkyl or cycloalkyl having from 1 to 6 carbon atoms or phenyl and the compound III obtained is then oxidized to a compound of formula I; or (b) a compound of formula IV

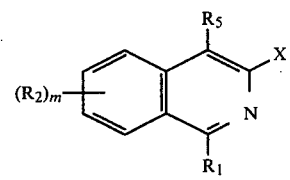

in which $R_5$ denotes methyl, hydroxymethyl or aminomethyl which may by substituted at the nitrogen atom by alkyl having from 1 to 4 carbon atoms and X, $R_1$, $R_2$ and m have the same meaning as in Formula I is oxidized to give a compound of formula I; or (c) a compound of formula V

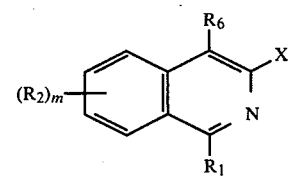

in which $R_6$ denotes cyano, carboxy, halocarboxy, or alkylcarboxy having from 1 to 7 carbon atoms and X, $R_1$, $R_2$ and m have the same meaning as in Formula I is reduced to a compound of formula I; or (d) a compound of formula VI

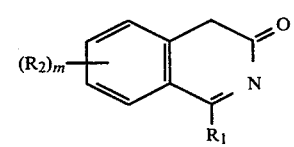

in which $R_1$, $R_2$ and m have the same meaning as in Formula I is reacted with a Vilsmeier complex compound to give a compound of formula I; or (e) a compound of formula VII

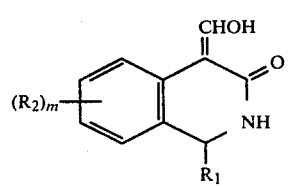

in which $R_1$, $R_2$ and m have the same meaning as in Formula I is reacted with an acid chloride, for example $POCl_3$ or $SOCl_2$, to give a compound of formula I; or (f) in a compound of formula I

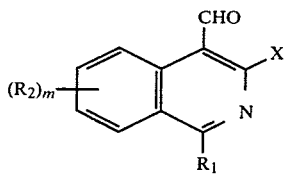

in which X, $R_2$ and m have the same meaning as in Formula I and $R_1$ denotes a phenyl ring this phenyl ring is subsequently substituted; or (g) a radical $R_2$ or a substituent in the 1-position at the phenyl ring is modified to obtain another compound of formula I.

The manufacture of starting compounds of formula II for process (a) is described in DE-OS No. 2,225,669 and in Acad. Sci. Hung 60 (1969), page 177. For this purpose a nitrile or an amide of the formula

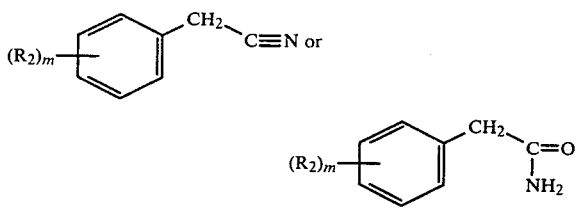

is reacted with an aldehyde of the formula

in phosphoric acid the content of phosphorus pentoxide of which can vary between that of 85% phosphoric acid and of polyphosphoric acid. The reaction is carried out at a temperature of from room temperature to 180° C., 80° to 110° C. being preferred. The further reaction according to Vilsmeier-Haack is carried out in known manner (cf. O. Bayer in Houben-Weyl: Methoden der organischen Chemie, 4th edition, Y. Thieme, Stuttgart 1954. volume 7/1, page 29). In this process compounds of formula II are reacted, for example with dimethyl formamide/phosphorus oxichloride or phosphorus oxibromide at a temperature of from 0° to 30° C. Suitable solvents are inert, anhydrous organic solvents such as chloroform, carbon tetrachloride, tetrahydrofurane, dioxane, benzene, toluene, chlorobenzene, or N,N-dimethyl formamide. The Vilsmeier complex compound is used in an at least equivalent amount, preferably in a three- to fivefold excess. The oxidation of compound III can be performed in usual manner. As oxidant potassium permanganate, chromic acid or manganese dioxide is used and the reaction is carried out in aqueous solution or in a heterogeneous system, the aqueous phase having a neutral to acid pH, preferably in the range of from 1 to 6. When operating in a heterogenous system, inert aprotic solvents that are immiscible with water can be used, for example benzene, toluene, chlorobenzene, chloroform or carbon tetrachloride.

According to process (b) the compounds of the invention are obtained by reacting a compound of formula IV with an oxidizing agent, for example manganese dioxide. Oxidation reactions of this type are known (cf. for example "Compendium of Organic Synthetic Methods" edited by John Wiley and Sons, Inc. (1971), pages 146 to 147 and 150 to 152).

Process (c) is likewise known per se. In this process a compound of formula V, carrying a carboxy group or an appropriate carboxy derivative in the 4-position, is reduced to a 4-formyl compound of formula I. Besides the carboxy group itself, the following carboxylic acid derivatives are suitable: esters, acid chlorides, acid anhydrides, acid amides, acid hydrazides, or nitriles. The transformation of the said functional groups into the formyl group is also known per se (cf. for example "Compendium of Organic Synthetic Methods", edited by John Wiley and Sons, Inc. (1971), pages 132 to 137, 148 to 150, 152 to 153 and 166 to 168).

In process (d) a compound of formula VI is reacted in known manner with a Vilsmeier-Haack complex compound as described for process (a). Starting compounds VI are obtained, for example, by a process analogous to that described in I. Heterocyclic Chem. 7, (1970), page 615.

In process (e) a compound of formula VII is transformed into a compound of the invention using phosphorus oxichloride or bromide in an at least equivalent amount, preferably in a three- to fivefold excess. Suitable solvents are inert aprotic solvents such as benzene, toluene, chlorobenzene, chloroform, or carbon tetrachloride. In general, the reaction is carried out at a temperature of from 30° to 100° C., preferably 50° to 80° C.

In process (f) the aromatic radical $R_1$ is liable to electrophilic substitution so that, generally, all substituents with which such a substitution is possible can be introduced into said ring. Suitable reactions are, above all, the halogenation, sulfonation or nitration, the latter being of particular interest. In this case, the compound of formula I is subjected to the usual nitration conditions (sulfuric acid, nitric acid, cooling with ice.

According to process (g) the substituent $R_2$ contained in a compound of formula I or subsequently introduced and the substituents of the radical $R_1$ can be modified whereby further compounds of formula I are formed.

From among a great number of possibilities a few examples are given. By reduction of an aromatic nitro group an amino compound is obtained, for example, in the case of $R_1$ being the 4-nitro benzene radical, the corresponding 4-aminophenyl compound. The reduction is carried out in usual manner, preferably by hydrogenation with a metal catalyst, for example Raney nickel, optionally in a solvent, for example in ethanol. A further example is the acylation or alkylation of an amino group. If $R_1$ denotes an aminophenyl radical, it can be transformed into the 4-acetylaminophenyl radical under the usual conditions, for example with acetanhydride in pyridine at low temperatures (0° to 10° C.). In the case of dimethyl sulfate, the methylamino or dimethylamino compound can be isolated. The diazotization of an aromatic amino group with subsequent reaction with a nucleophilic group is a further possibility to modify substituents of a compound of formula I. With nitrous acid (usually prepared from sodium nitrite and sulfuric acid), for example, a radical $R_1$ denoting the 4-aminophenyl group can be transformed at low temperatures (0° to 5° C.) into the corresponding diazonium salt which then yields the 4-chlorophenyl radical with hydrochloric acid in the presence of copper chloride or the 4-hydroxyphenyl radical by boiling. The splitting of an alkoxy group to the corresponding hydroxy compound constitutes another method to transform the various substituents. Thus, the ether splitting of a 7-methoxy compound ($R_2=OCH_3$), for example with hydrogen bromide in aqueous acetic acid at a temperature of from 50° C. to 120° C. yields the corresponding 7-hydroxy compound. The oxidation of a methyl group to the carboxy group and the transformation of a carboxy group into the amino group are also worth mentioning.

The compounds of the invention have valuable pharmacological properties, in the first place they have a therapeutic effect on the central nervous system. They inhibit spasms caused by the electric current and show a prolongation of narcosis induced by thiopental. The compounds of the invention can, therefore, be used as active substances in antispasmodic or tranquilizing medicaments. The novel compounds can be used either alone or in admixture with physiologically tolerated adjuvants or carriers. For oral administration the active compounds are mixed with the usual substances and from the mixtures the usual forms of preparation are produced, for example, tablets, push-fit capsules, aqueous, alcoholic or oily suspensions or aqueous, alcoholic or oily solution. Suitable inert carrier materials are, for example magnesium carbonate, lactose or corn starch with the addition of other substances, for example magnesium stearate. The preparations can be produced in the form of dry as well as moist granules. As oily adjuvants or solvents vegetable and animal oils can be used, such as sunflower oil or cod-liver oil.

A special mode of administration is the intravenous injection. To this end the active compounds or their physiologically tolerated salts are dissolved in the usual solvents. Physiologically tolerated salts are formed, for example, with the following acids: hydrochloric, hydrobromic and hydroiodic acid, phosphoric acid, sulfuric acid, methylsulfuric acid, amidosulfonic acid, nitric acid, formic acid, acetic acid, propionic acid, succinic acid, tartaric acid, lactic acid, malonic acid, fumaric acid, maleic acid, oxalic acid, citric acid, malic acid, mucic acid, benzoic acid, salicylic acid, aceturic acid, embelic acid naphthalene-1,5-disulfonic acid, ascorbic acid, phenylacetic acid, p-aminosalicylic acid, hydroxyethanesulfonic acid, benzenesulfonic acid or synthetic resins containing acid groups, for example those having an ion exchange effect. Solvents for the physiologically tolerated salts of the active compounds for an intravenous administration are, for example, water, physiological sodium chloride solution and alcohols, for example, ethanol, propanediol or glycerol, as well as sugar solutions, for example glucose or mannitol solutions, or a mixture of the various solvents mentioned.

The compounds of formula I can also be used as intermediates for the manufacture of isoquinoline derivatives, for example those carrying a basic substituent in 3-position.

The following examples illustrate the invention.

EXAMPLE 1

3-Chloro-1-phenyl-isoquinoline-4-aldehyde 95 g of potassium permanganate are slowly added in 5 gram portions at room temperature to a solution of 296 g of 3-chloro-4-dimethylaminomethylene-1-phenyl-isoquinoline in 4 l of 2N $H_2SO_4$. The temperature is maintained below 30° C. by cooling. Stirring of the mixture is continued for 2 hours at room temperature and the precipitated aldehyde is filtered off with suction. After drying and redissolution from ethyl acetate, 290 g of aldehyde melting at 170° to 172° C. are isolated, which corresponds to a yield of 90%.

The starting compound can be prepared in the following manner:

146 g of phosphorus oxichloride are added dropwise to 73 ml of N,N-dimethylformamide and 400 ml of tetrahydrofurane at a rate such that the temperature does not exceed ±25° C. Stirring of the mixture is continued for 20 minutes at room temperature, whereupon 56 g (0.25 mol) of 1-phenyl-1,4-dihydro-3-(2H)-isoquinoline are added while cooling in a manner such that a temperature remains in the range of from 20° to 35° C. Stirring is continued for 3 hours at room temperature and then the reaction solution is added to a mixture of 1 l of 2N NaOH and 3.5 kg of ice. The mixture is repeatedly extracted with a total amount of toluene of 1.5 l. The toluene phase is washed with water, dried and the solvent is removed under reduced pressure. After rubbing of the residue with ether, 53 g of crystalline product melting at 111° to 118° C. are filtered off, corresponding to a yield of 71% of the theory.

EXAMPLE 2

3-Chloro-6,7-dimethoxy-1-phenyl-isoquinoline-4-aldehyde 6,7-Dimethoxy-1-phenyl-1,4-dihydro-3-(2H)-isoquinoline are reacted as described in Example 1. After recrystallization from ethyl acetate, a crystalline product melting at 208° to 210° C. is obtained in a yield of 35%.

EXAMPLE 3

3-Chloro-1-(4-chlorophenyl)-6,7-dimethoxy-isoquinoline-4-aldehyde

M.p. 263°–265° C.
Yield 27%

EXAMPLE 4

3-Chloro-1-(4-chlorophenyl)-isoquinoline-4-aldehyde

M.p. 192°–193° C.
Yield 37%

EXAMPLE 5

3-Chloro-1-(2,4-dichlorophenyl)-isoquinoline-4-aldehyde

M.p. 192°–193° C.
Yield 32%

EXAMPLE 6

3,6-Dichloro-1-phenyl-isoquinoline-4-aldehyde

M.p. 166°–171° C.
Yield 48%

EXAMPLE 7

3-Chloro-1-(2-methylphenyl)-isoquinoline-4-aldehyde

M.p. 140°–142° C.
Yield 37%

EXAMPLE 8

3-Chloro-1-(3-chlorophenyl)-isoquinoline-4-aldehyde 199 g of phosphorus oxichloride are added dropwise to a solution of 99 g of N,N-dimethyl formamide in 400 ml of tetrahydrofuran at a rate such that the temperature does not exceed 5° C. Stirring is continued for 20 minutes at room temperature. Next, 87.7 g of 1-(3-chlorophenyl)-1,4-dihydro-3-(2H)-isoquinolinone are added in portions at 0° C. After a 2 hour stirring at 0° to 5° C., the reaction solution is poured into a mixture of 1.95 l of 2N NaOH, 6 kg of ice and 1 l of toluene. The toluene phase is separated, washed twice with water and added to 1.3 l of acetone and 1.3 l of 2N $H_2SO_4$. 38.8 g of carefully pulverized potassium permanganate are added in portions and at 20° C. to the heterogeneous mixture obtained and the mixture is stirred for 6 hours. The toluene phase is separated, washed successively with water, 2N NaOH and again with water, dried, filtered and the solvent is removed under reduced pressure.

Yield 46% m. p. 169°–171° C.

EXAMPLE 9

3-Chloro-1-(pyrid-4-yl)-isoquinoline-4-aldehyde

M.p. 154°–159° C.
Yield 33%

EXAMPLE 10

3-Chloro-1-(4-fluorophenyl)-isoquinoline-4-aldehyde

M.p. 217°–218° C.
Yield 42%

EXAMPLE 11

3-Chloro-1-phenyl-isoquinoline-4-aldehyde

In an atmosphere of argon and at −5° C. 10.7 ml of a 20% diisobutylaluminum hydride solution in toluene are slowly added dropwise to 2.64 g of 3-chloro-4-cyano-1-phenyl-isoquinoline in 150 ml of absolute toluene. The mixture is stirred for 10 minutes at 0° C. and then hydrolized with a small amount of glacial acetic acid until the reaction is weakly acid. Next, water is added and the toluene phase is separated. The organic phase is washed successively with saturated sodium bicarbonate solution and with water, dried and the solvent is removed under reduced pressure. The residue is rubbed with ether and recrystallized from ethyl acetate.

Yield 85% m.p. 170°–172° C.

EXAMPLE 12

3-Chloro-1-phenyl-isoquinoline-4-aldehyde

A mixture of 2.69 g of 3-chloro-1-phenyl-isoquinoline-4-hydroxymethylene in 50 ml of chloroform and 1 g of activated manganese dioxide is stirred for 3 hours at room temperature. The solution is filtered and the solvent removed under reduced pressure. After redissolution from ethyl acetate, the residue melts at 170°–171° C. 1.4 g are obtained.

EXAMPLE 13

3-Chloro-1-(3-nitrophenyl)-isoquinoline-4-aldehyde 5.4 g of 3-chloro-1-phenyl-isoquinoline-4-aldehyde are slowly added at 0° C. to 30 ml of concentrated sulfuric acid and 1.65 ml of 65% nitric acid. The solution is stirred for 2 hours at 5° C. and then poured into 600 ml of water. The precipitate is filtered off, thoroughly washed with water and, after drying, it is recrystallized from ethyl acetate.

3.4 g of aldehyde melting at 200° to 202° C. are isolated.

What is claimed is:

1. Isoquinoline 4-aldehyde of the formula

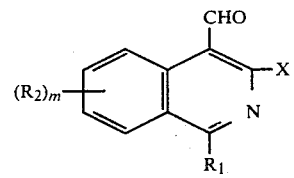

in which X denotes bromine or chlorine,
$R_1$ is phenyl or phenyl mono- or disubstituted by halogen, hydroxy, nitro alkyl or alkoxy each having from 1 to 6 carbon atoms, benzoyloxy, trifluoromethyl, amino or amino substituted by one or two alkyl groups having from 1 to 4 carbon atoms or is pyridyl or thienyl;
$R_2$ is hydrogen, halogen, hydroxy, alkyl or alkoxy having from 1 to 6 carbon atoms, nitro, amino, benzyloxy, methylene dioxy or ethylene dioxy and m is 1 or 2;

or the physiologically tolerated salts thereof.

2. The compound defined in claim 1 wherein X is chlorine, $R_1$ is pyridyl or phenyl wherein said phenyl is mono- or disubstituted by hydroxy, halogen, nitro, alkyl or alkoxy of from 1 to 4 carbon atoms, amino or amino substituted by two alkyl groups having from 1 to 4 carbon atoms, and $R_2$ is hydrogen, halogen, alkyl or alkoxy of from 1 to 4 carbon atoms, or hydroxy.

3. The compound defined in claim 1 in which X is chlorine, $R_1$ is phenyl mono- or disubstituted by halogen, hydroxy, nitro, alkyl of 1 to 3 carbon atoms, amino or methoxy and $R_2$ is hydrogen, halogen, hydroxy, alkyl of 1 to 3 carbon atoms or methoxy.

4. The compound of claim 1 which is 3-chloro-1-phenyl-isoquinoline-4-aldehyde.

5. The compound of claim 1 which is 3-chloro-6,7-dimethoxy-1-phenyl-isoquinoline-4-aldehyde.

6. The compound of claim 1 which is 3-chloro-1-(2-methylphenyl)-isoquinoline-4-aldehyde.

7. The compound of claim 1 which is 3-chloro-1-(4-fluorophenyl)-isoquinoline-4-aldehyde.

8. The compound of claim 1 which is 3-chloro-1-(2-fluorophenyl)-isoquinoline-4-aldehyde.

* * * * *